US010059914B2

(12) United States Patent
Watkins et al.

(10) Patent No.: US 10,059,914 B2
(45) Date of Patent: Aug. 28, 2018

(54) DISPOSABLE BIOREACTORS AND METHODS FOR CONSTRUCTION AND USE THEREOF

(71) Applicant: Distek, Inc., North Brunswick, NJ (US)

(72) Inventors: Jeff Watkins, Watchung, NJ (US); Jeffrey Brinker, Westfield, NJ (US)

(73) Assignee: Distek, Inc., North Brunswick, NJ (US)

( * ) Notice: Subject to any disclaimer, the term of this patent is extended or adjusted under 35 U.S.C. 154(b) by 73 days.

(21) Appl. No.: 15/038,194

(22) PCT Filed: Nov. 21, 2014

(86) PCT No.: PCT/US2014/066977
§ 371 (c)(1),
(2) Date: May 20, 2016

(87) PCT Pub. No.: WO2015/077663
PCT Pub. Date: May 28, 2015

(65) Prior Publication Data
US 2016/0281043 A1  Sep. 29, 2016

Related U.S. Application Data

(60) Provisional application No. 61/907,146, filed on Nov. 21, 2013.

(51) Int. Cl.
C12M 1/00 (2006.01)
C12M 3/00 (2006.01)
(Continued)

(52) U.S. Cl.
CPC ............ *C12M 23/28* (2013.01); *C12M 23/14* (2013.01); *C12M 23/46* (2013.01); *C12M 27/02* (2013.01);
(Continued)

(58) Field of Classification Search
CPC ...... C12M 23/14; C12M 23/28; C12M 23/46; C12M 27/02; C12M 29/04; C12M 41/12; C12M 41/32; C12N 1/00
See application file for complete search history.

(56) References Cited

U.S. PATENT DOCUMENTS 6,245,555 B1 * 6/2001 Curtis .................... C12M 23/26
  220/495.05
7,384,783 B2 * 6/2008 Kunas et al. ........... B01F 7/001
  435/289.1
(Continued)

FOREIGN PATENT DOCUMENTS

EP  2141224 A1  1/2010
GB  2202549 A   9/1988
(Continued)

OTHER PUBLICATIONS

International Preliminary Report on Patentability and Written Opinion; dated May 24, 2016 for PCT Application No. PCT/US2014/066977.
(Continued)

*Primary Examiner* — Gautam Prakash
(74) *Attorney, Agent, or Firm* — Mendolsohn Dunleavy, P.C.; Steve Mendelsohn

(57) ABSTRACT

In one embodiment, a disposable bioreactor including a headplate and a stirrer. The headplate has at least one inlet port aperture and one outlet port aperture formed therein and is adapted to couple sealingly with a bag capable of receiving a culture medium. The stirrer is coupled to and extends from the headplate and is adapted to stir the culture medium when the headplate is coupled to the bag. The bioreactor is adapted to fit within the upper opening of the stand of an existing conventional glass bioreactor, so that the bag is suspended within the vessel.

20 Claims, 8 Drawing Sheets

(51) Int. Cl.
 *C12M 1/34* (2006.01)
 *C12M 1/06* (2006.01)
 *C12N 1/00* (2006.01)

(52) U.S. Cl.
 CPC ............ *C12M 29/04* (2013.01); *C12M 41/12* (2013.01); *C12M 41/32* (2013.01); *C12N 1/00* (2013.01)

(56) References Cited

U.S. PATENT DOCUMENTS

| | | |
|---|---|---|
| 2003/0129743 A1 | 7/2003 | Wildi et al. |
| 2009/0311776 A1 | 12/2009 | Kelly, Jr. et al. |
| 2011/0038222 A1* | 2/2011 | Ludwig et al. ..... B01F 3/04269 366/102 |
| 2011/0058447 A1* | 3/2011 | Reif et al. ............ B01F 7/1695 366/249 |

FOREIGN PATENT DOCUMENTS

| | | |
|---|---|---|
| JP | 2007282629 A | 11/2007 |
| WO | WO03006633 A1 | 1/2003 |

OTHER PUBLICATIONS

International Search Report and Written Opinion; dated Feb. 16, 2015 for PCT Application No. PCT/US2014/066977.
English Translation of Claims and Figure Labels for JP4986659B2.

\* cited by examiner

DISPOSABLE BIOREACTORS AND METHODS FOR CONSTRUCTION AND USE THEREOF

FIELD OF THE INVENTION

The present invention relates generally to the growth of biological cultures and, in particular, to bioreactors for biologically-active substances.

BACKGROUND OF THE INVENTION

A bioreactor is a vessel or container used for the growth of biological cultures, such as cells, bacteria, yeasts, or fungi. These cultures are used to produce a variety of biologically-active substances, including pharmaceuticals, fragrances, fuel, and the like.

A conventional bioreactor vessel has a cylindrical shape and includes a mixing apparatus, means for introducing a gas supply, and a temperature control system. Most bioreactor applications require a sterilization process to ensure that the process run does not yield the growth of, or contamination from, undesirable biological organisms. Traditional methods of sterilizing bioreactors include the use of an autoclave (for smaller vessels) or a steam sterilization-in-place process (for larger vessels). In recent years, there has been an introduction of single-use bioreactors. A conventional single-use bioreactor is typically delivered to the end user in the form of a pre-sterilized container and is used for only a single process run, after which the user disposes of the single-use bioreactor.

Typical materials of construction for small autoclavable bioreactor vessels may include, e.g., a glass vessel with a stainless steel cover, tube, and sensor adapters, mixing apparatus, and baffles. These vessels are filled with culture media and are then carried to an autoclave, where they are sterilized for several hours. The vessel is then taken back to the laboratory, where it is allowed to cool down. The vessel is then connected to a control system, which is used to control temperature, agitation, aeration and pH. The vessel is subsequently inoculated with the desired organism, at which time the process run proceeds.

While this has been the method of choice for process development for the last half century, the problem with this method is that the process is very time- and labor-consuming. Each process run typically lasts 1 to 10 days. Between each run, the vessel must be manually cleaned and sterilized in the autoclave. This can result in a turnaround time of 1 to 3 days between runs. As a result, the single-use bioreactor was developed to allow the end user to eliminate the sterilization and cleaning portion of the process. At the end of each run, the vessel is discarded, and a new pre-sterilized vessel is removed from the packaging and is set up to start the next run.

A typical single-use bioreactor employs a medical-type bag that rests on top of a platform, where an orbital or rocking motion is induced to mix and aerate the organism. However, a problem with this type of system is that the mixing action and oxygen transfer are limited, resulting in a low organism growth density relative to the design of a traditional agitator and sparger (a device that bubbles gas through the bioreactor) in a "stirred tank" bioreactor. In addition, the different mixing motion and bag geometry in the medical-type bag bioreactor does not lend itself to be scaled up to larger production processes. Further, in order for a scientist to use one of the medical-type bag single-use rocking systems, the scientist is required to invest substantial capital and laboratory space in an additional piece of specialized equipment.

These limitations of the initial single-use bioreactor designs have led to the development of "stirred-tank" single-use bioreactor products.

One type of stirred-tank single-use bioreactor product employs a bag-type vessel containing a mixer, sparger, sensors, and tubing. The bag is placed into a structure of some type (typically a stainless cylinder) and conforms to its shape. The intent is for the bag to mimic a traditional stainless-steel or glass stirred-tank bioreactor. However, the design does not lend itself to small vessel sizes (e.g., less than 50 L), because the size of the fittings in the bag and the number of fittings for a standard bioreactor exceed the allowable accessible surface area on the bag.

Another type of stirred-tank single-use bioreactor product employs a rigid plastic vessel that is self-supporting and has a self-contained mixing apparatus, aeration system, and sensors. This type of unit mimics the look and feel of a traditional stainless-steel or glass-type bioreactor vessel. However, unlike a single-use bag system, the rigid plastic used in this design cannot be folded or reduced in size for storage or disposal. This burdens the end user with a requirement for a large environmentally-controlled area within the user's facility for storage of future vessels, as well as increased disposal costs associated with such larger, non-compressible vessels.

SUMMARY

Embodiments of the present invention solve the foregoing problems and provide additional benefits by employing a single-use, disposable bioreactor apparatus and related methods for its construction and use.

In one embodiment, the present invention provides a bioreactor including a headplate and a stirrer. The headplate has at least one inlet port aperture and one outlet port aperture formed therein and is adapted to couple sealingly with a bag capable of receiving a culture medium. The stirrer is coupled to and extends from the headplate and is adapted to stir the culture medium when the headplate is coupled to the bag.

In another embodiment, the present invention provides a method for using a bioreactor. The method includes: sealingly coupling, to a headplate, a bag capable of receiving a culture medium, wherein the headplate has at least one inlet port aperture and one outlet port aperture formed therein; and stifling the culture medium using a stirrer coupled to the headplate.

In a further embodiment, the present invention provides a bioreactor including: a headplate (i) having at least one inlet port aperture and one outlet port aperture formed therein and (ii) adapted to couple sealingly with a bag capable of receiving a culture medium; a stirrer coupled to and extending from the headplate; at least one inlet tube passing through the inlet port aperture and at least one outlet tube passing through the output port aperture; a dissolved oxygen sensor coupled to and extending from the headplate; a temperature sensor coupled to and extending from the headplate; a pH sensor coupled to and extending from the headplate; an exhaust port coupled to a filter extending from the headplate; a sparger port coupled to a filter extending from the headplate; and at least one length of coiled tubing passing through one of the apertures formed in the headplate.

DETAILED DESCRIPTION

Figure 1:
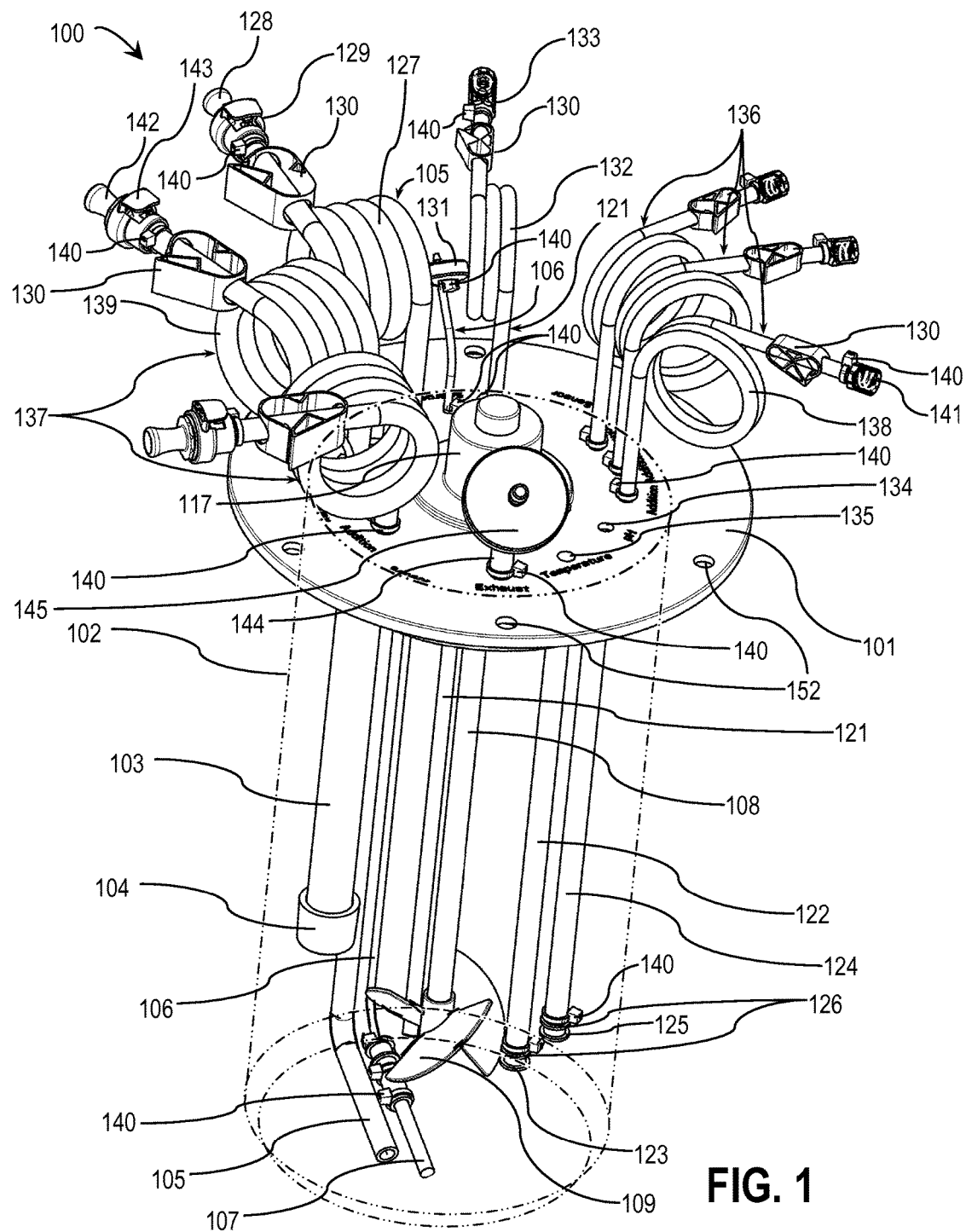
FIG. 1 shows a top-side perspective view of a disposable bioreactor consistent with one embodiment of the invention.
Figure 2:
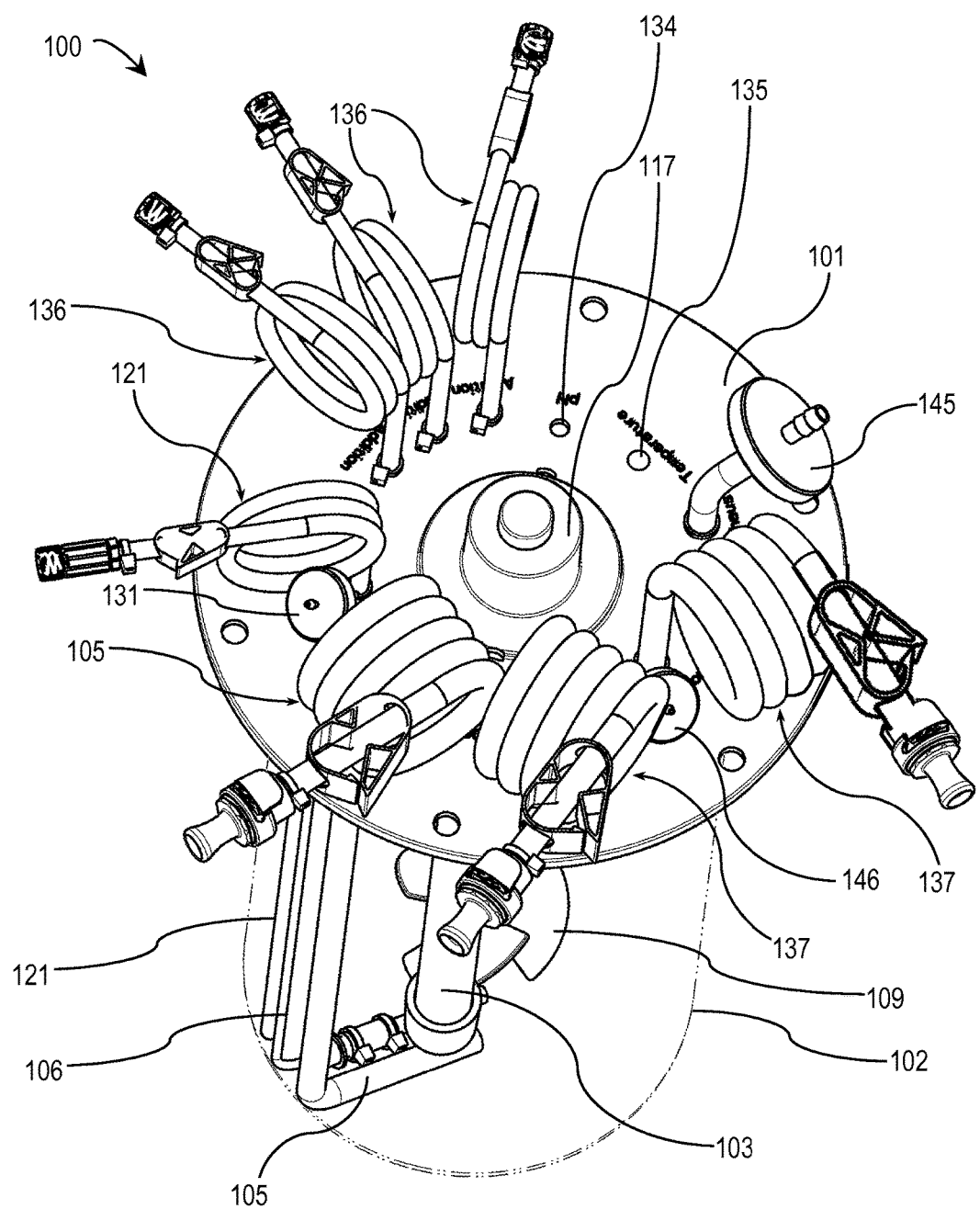
FIG. 2 shows a top perspective view of the disposable bioreactor of FIG. 1.
Figure 3:
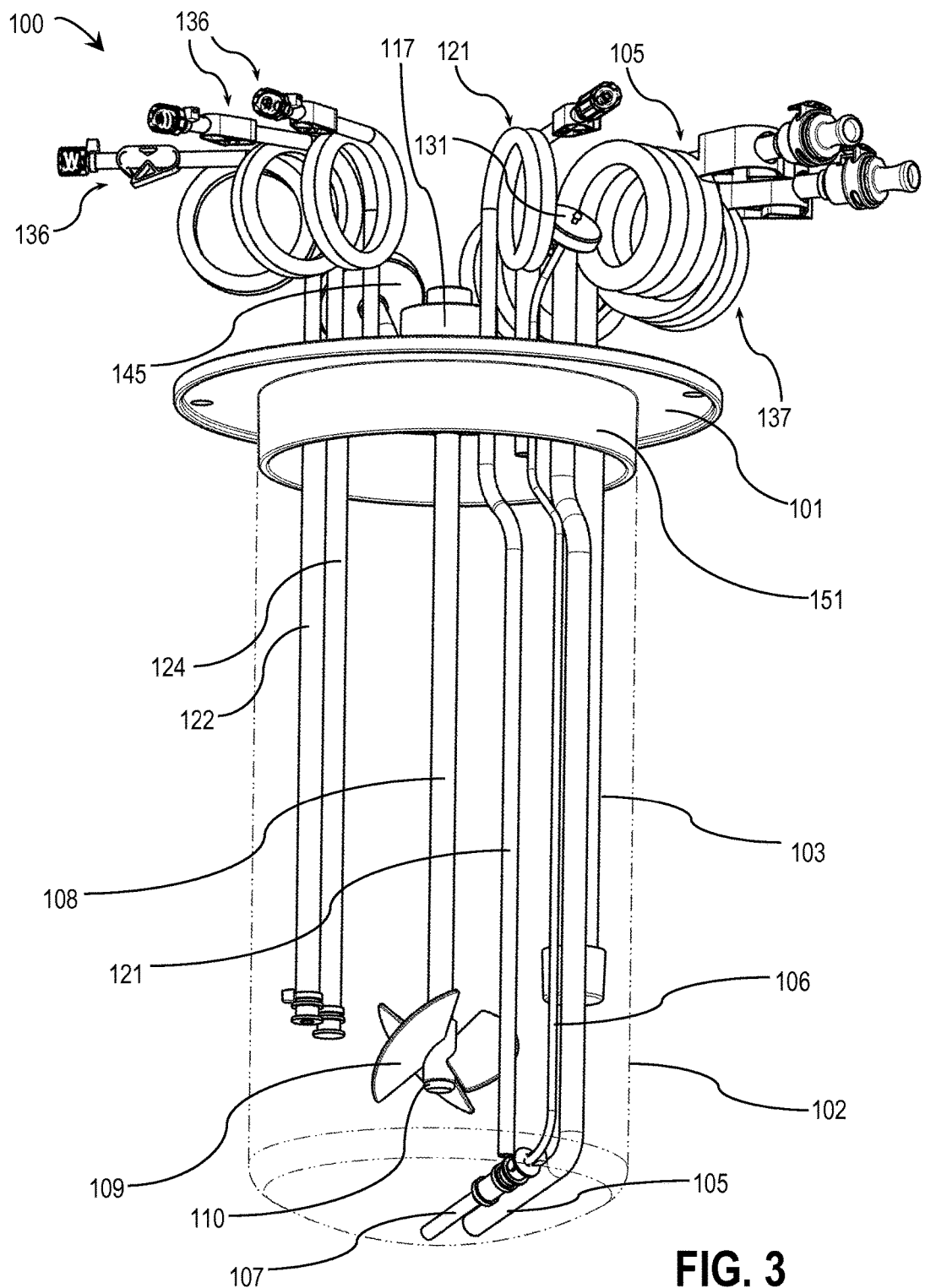
FIG. 3 shows a side perspective view of the disposable bioreactor of FIG. 1.

With reference to FIGS. 1-6, a disposable bioreactor 100 consistent with one embodiment of the invention is illustrated. The features described below are generally visible in FIG. 1, unless otherwise indicated.

Bioreactor 100 includes a circular headplate 101 that serves as a support for a vessel liner 102 (shown in broken lines). Vessel liner 102 is a flexible bag in which a culture medium is disposed, and in which organisms are grown in the culture medium. These organisms may be submerged (e.g., suspended or immobilized) in a liquid medium disposed within vessel liner 102, or attached to the surface of a solid medium disposed within vessel liner 102.

Headplate 101 also serves as a support for various additional components mounted on and through headplate 101. These additional components may vary in different embodiments of the invention. In this embodiment, the additional components include the following:

A dissolved oxygen (DO) sensor (not shown) is housed within DO tubing 103, which is a length of platinum-cured silicon tubing that passes through headplate 101 and has a probe cover 104 at its bottom end. DO probe (not shown) may be, e.g., a galvanic (electrochemical) dissolved oxygen sensor, an optical sensor, or another type of sensor that detects dissolved oxygen in the culture medium disposed within vessel liner 102. DO tubing 103 houses wiring (not shown) that couples DO probe (not shown) to a manual or automatic monitoring mechanism, transmitter, processor, or the like, via an interface (not visible in the figures) disposed on the upper surface of headplate 101.

A cell harvest tube 105 is formed from a length of platinum-cured silicon or weldable TPE tubing that passes through headplate 101. Cell harvest tube 105 has, at its bottom end, an open tip that may be tapered and is desirably disposed as close to the bottom of vessel liner 102 as possible, to maximize harvesting of cells. The other end of cell harvest tube 105 is coupled to a manual or automatic pump or pipetting mechanism, or the like, via a coiled portion 127 that permits extension of cell harvest tube 105 to a length of approximately 76 cm. and includes a tubing clamp 130 near its free end. To enable such coupling of cell harvest tube 105, the free end of coiled portion 127 leads to a male MPC-type sealing plug 128 mounted to coiled portion 127 via an MPC-type hose barb non-valved in-line coupling body 129. Coupling body 129 is secured to the free end of coiled portion 127 using a standard wire tie 140, which is also the case with most other tubing connections of bioreactor 101, as seen throughout FIGS. 1-4.

A sparger tube 106 is formed from a length of platinum-cured silicon tubing that passes through headplate 101. At its upper end, sparger tube 106 is coupled to a gas supply via a validatable inlet filter 131 disposed inline at the upper end of sparger tube 106. The other (i.e., bottom) end of sparger tube 106 is securely coupled to a polyethylene micro-sparger 107, which is disposed near the bottom of vessel liner 102 and bubbles a chemically-inert gas through the culture medium disposed within vessel liner 102. Standard wire ties 140 are used to secure inlet filter 131 to the free end of sparger tube 106, and also to secure inlet filter 131 to headplate 101.

A sampling tube 121 is formed from a length of platinum-cured silicon or weldable TPE tubing that passes through headplate 101. Sampling tube 121 permits samples of the culture medium to be removed for analysis and has, at its bottom end, an open tip that may be tapered. The other end of sampling tube 121 is coupled to a manual or automatic pump or syringe mechanism, or the like, via a coiled portion 132 that permits extension of sampling tube 121 to a length of approximately 51 cm. and includes a tubing clamp 130 near its free end. To enable such coupling of sampling tube 121, the free end of coiled portion 132 leads to a needleless male luer-type connector 133 mounted to coiled portion 132. Standard wire ties 140 are used to secure male luer-type connector 133 to the free end of sampling tube 121, and also to secure sampling tube 121 to headplate 101.

A sensor tube 122 is formed from a length of platinum-cured silicon tubing that passes through headplate 101. Sensor tube 122 has a non-invasive pH or DO sensor 123 mounted at its bottom end by means of a plug insert 126, secured using a standard wire tie 140. Sensor tube 122 houses wiring (not shown) that couples the pH or DO sensor 123 to a manual or automatic monitoring mechanism, transmitter, processor, or the like, via a pHor DO interface 134 disposed on the upper surface of headplate 101.

A temperature sensor tube 124 is formed from a length of platinum-cured silicon tubing that passes through headplate 101. Temperature sensor tube 124 has a temperature sensor 125 seated at its bottom end by means of a plug insert 126. Temperature sensor tube 124 houses wiring (not shown) that couples temperature sensor (not shown) to a manual or automatic monitoring mechanism, transmitter, processor, or the like, via a temperature interface 135 disposed on the upper surface of headplate 101.

Three smaller addition tubes 136 and two larger addition tubes 137 (e.g., for introducing liquids into the culture medium) are formed from lengths of platinum-cured silicon or weldable TPE tubing that passes through headplate 101. At their bottom ends, each of addition tubes 136, 137 leads to a respective aperture (or short length of tubing) on the underside of headplate 101. The top ends of each addition tube 136 can be coupled to a manual or automatic pump or pipetting mechanism, or the like, via respective coiled portions 138, 139 that permit extension of addition tubes 136, 137 to lengths of approximately 51 cm. and approximately 76 cm, respectively. Each coiled portion 138, 139 includes a tubing clamp 130 near its free end. The free end of each coiled portion 138 of smaller addition tubes 136 leads to a respective needleless male luer-type connector 141 mounted to coiled portion 138. Standard wire ties 140 are used to secure male luer-type connector 141 to the free end of smaller addition tubes 136, and also to secure smaller addition tubes 136 to headplate 101. The free end of each coiled portion 139 of larger addition tubes 137 leads to a respective male MPC-type sealing plug 142 mounted to coiled portion 139 via an MPC-type hose barb non-valved in-line coupling body 143. Standard wire ties 140 are used to secure coupling body 143 to the free end of larger addition tubes 137, and also to secure larger addition tubes 137 to headplate 101.

A gas addition port (not visible in the figures) consisting of an aperture (or short length of tubing) on the underside of headplate 101 leads to a short length of platinum-cured silicon gas-addition tubing (not visible in the figures) that passes through headplate 101. A validatable inlet filter 146 (shown in FIG. 2) is disposed inline at the upper end of gas-addition tubing 144. A standard wire tie (not visible in the figures) is used to secure inlet filter 146 to the free end of the gas-addition tubing, and also to secure the gas-addition tubing to headplate 101.

An exhaust port (not visible in the figures) consisting of an aperture on the underside of headplate 101 leads to a short length of platinum-cured silicon exhaust tubing 144 that passes through headplate 101. A validatable inlet filter 145 is disposed inline at the upper end of exhaust tubing 144. A standard wire tie 140 is used to secure inlet filter 145 to the free end of exhaust tubing 144, and also to secure exhaust tubing 144 to headplate 101.

A stifling mechanism is formed from a shaft 108 rotatably mounted to headplate 101, with an impeller 109 mounted at the bottom end of shaft 108. Impeller 109, which has three generally semi-circular pitched blades, is secured to the end of shaft 108 via an o-ring 110 (shown in FIGS. 3 and 4). In alternative embodiments, shaft 108 may be foldable, telescoping, or in multiple hinged or otherwise joinable portions, to permit compact storage and transport.

Figure 5:
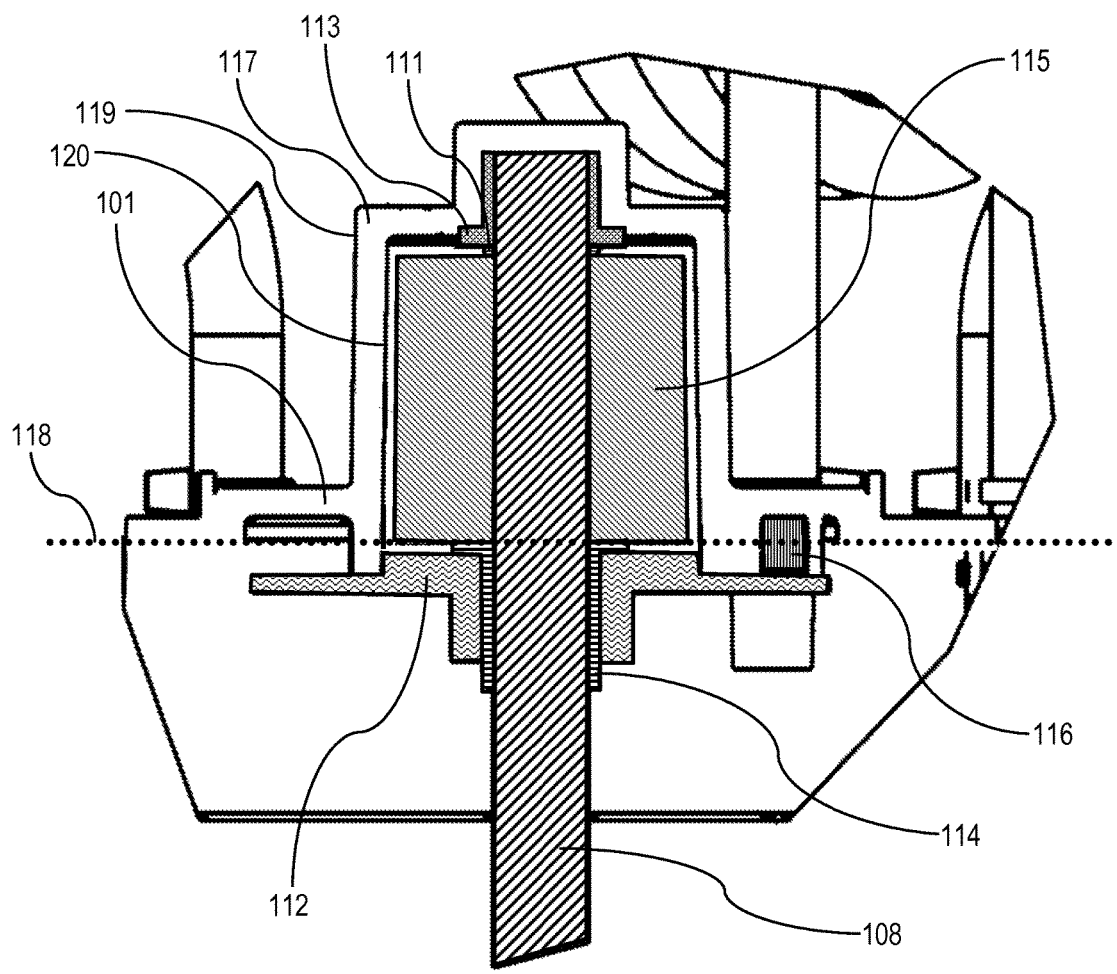
FIG. 5 shows a partial cross-sectional view of a portion of the disposable bioreactor of FIG. 1.

FIG. 5 is a partial cross-sectional view showing details of the interface between shaft 108 and headplate 101, which includes a magnetic drive assembly for impeller 109 to stir the culture medium. In FIG. 5, broken line 118 represents, generally, the plane of the culture medium-facing side (i.e., underside) of headplate 101. As shown, a permanent magnet 115 is coupled to shaft 108, and both shaft 108 and magnet 115 are disposed to freely rotate in tandem within the structure of an upper bearing 113 and a lower bearing 114 that capture shaft 108. A generally-cylindrical extended portion 117 is formed in headplate 101 to provide clearance for the magnetic drive assembly, while desirably maintaining magnet 115 above headplate 101.

Shaft 108 is rotatably disposed within bearings 113, 114, with magnet 115 disposed between upper bearing 113 and lower bearing 114 and rotating within but not contacting the interior surface 120 of generally-cylindrical extended portion 117.

Figure 4:
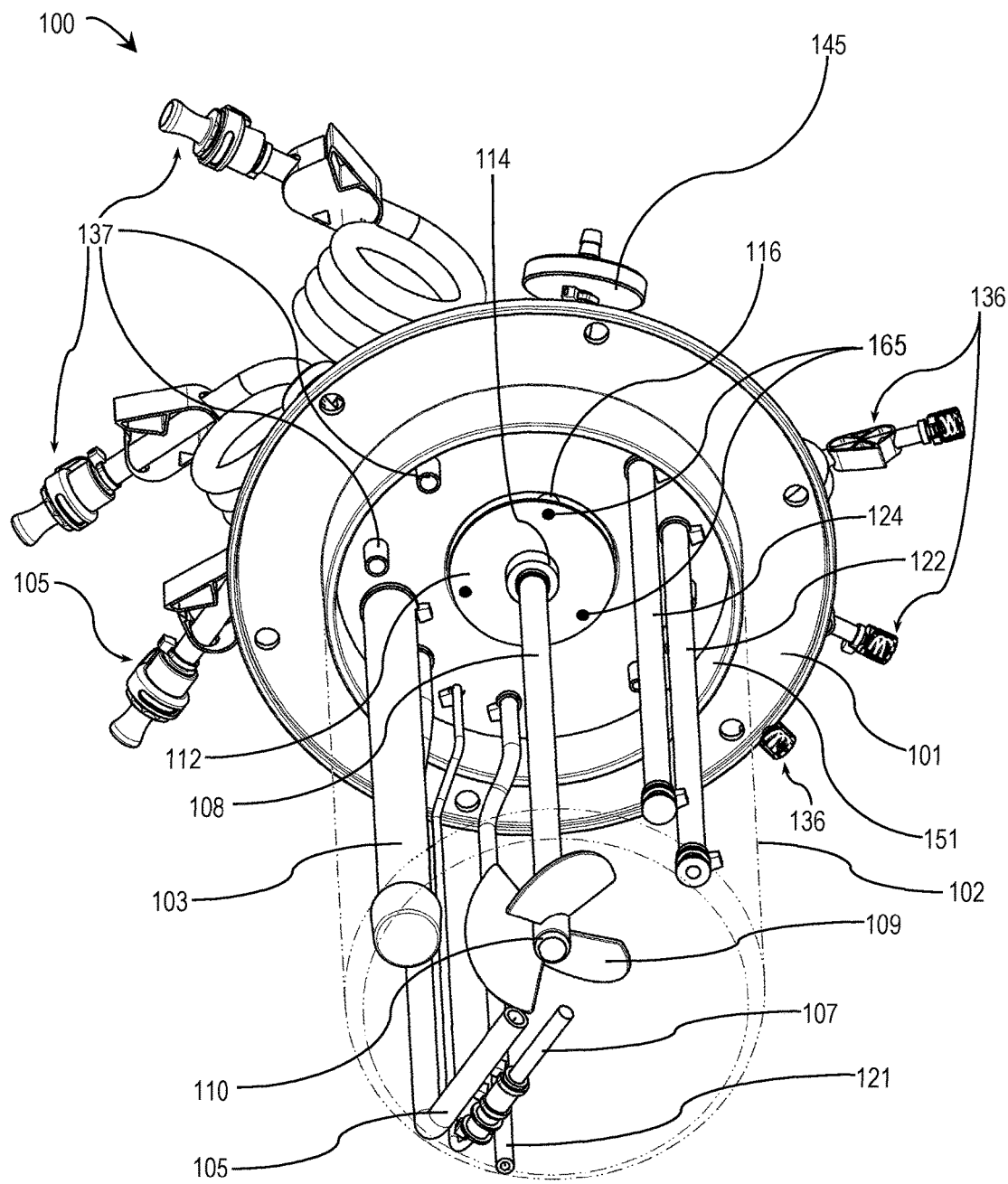
FIG. 4 shows a bottom perspective view of the disposable bioreactor of FIG. 1.

Bearings 113 and 114 are desirably polymer bearings that are self-lubricating. During the molding step of the fabrication of bearings 113, 114, solid lubricants are embedded within reinforcing fibers of the bearings. These solid lubricants reduce friction and enhance wear resistance of bearings 113, 114, which form a dry-running surface for shaft 108 to rotate in the magnetic field of magnet 115 while supported by bearings 113, 114. A retaining ring 111 is disposed on shaft 108 above magnet 115 to position shaft 108 within extended portion 117. Lower bearing 114 is supported by a drive retention bracket 112, which is coupled to headplate 101 via three screws 165 (shown in FIG. 4). Each screw 165 (or bolt, or other fastener) is driven through drive retention bracket 112, a respective press-fit expansion insert 116 (only one of which is shown in FIGS. 4 and 5), and headplate 101.

The exterior surface 119 of extended portion 117 is adapted to receive a driving assembly (not shown) having a recessed portion that matches the contours of exterior surface 119 of extended portion 117. The driving assembly employs a motor-driven drive magnet that rotates around portion 117 to cause magnet 115 to spin in synchronization. The attraction of the motor-driven drive magnet and magnet 115 passes substantially all or nearly all of the torque of the motor onto shaft 108. Accordingly, the driving assembly remains isolated from the culture medium inside vessel liner 102 and from the magnetic drive assembly of bioreactor 100, thereby eliminating potential hazards from leakage associated with shaft seals.

Figure 6:
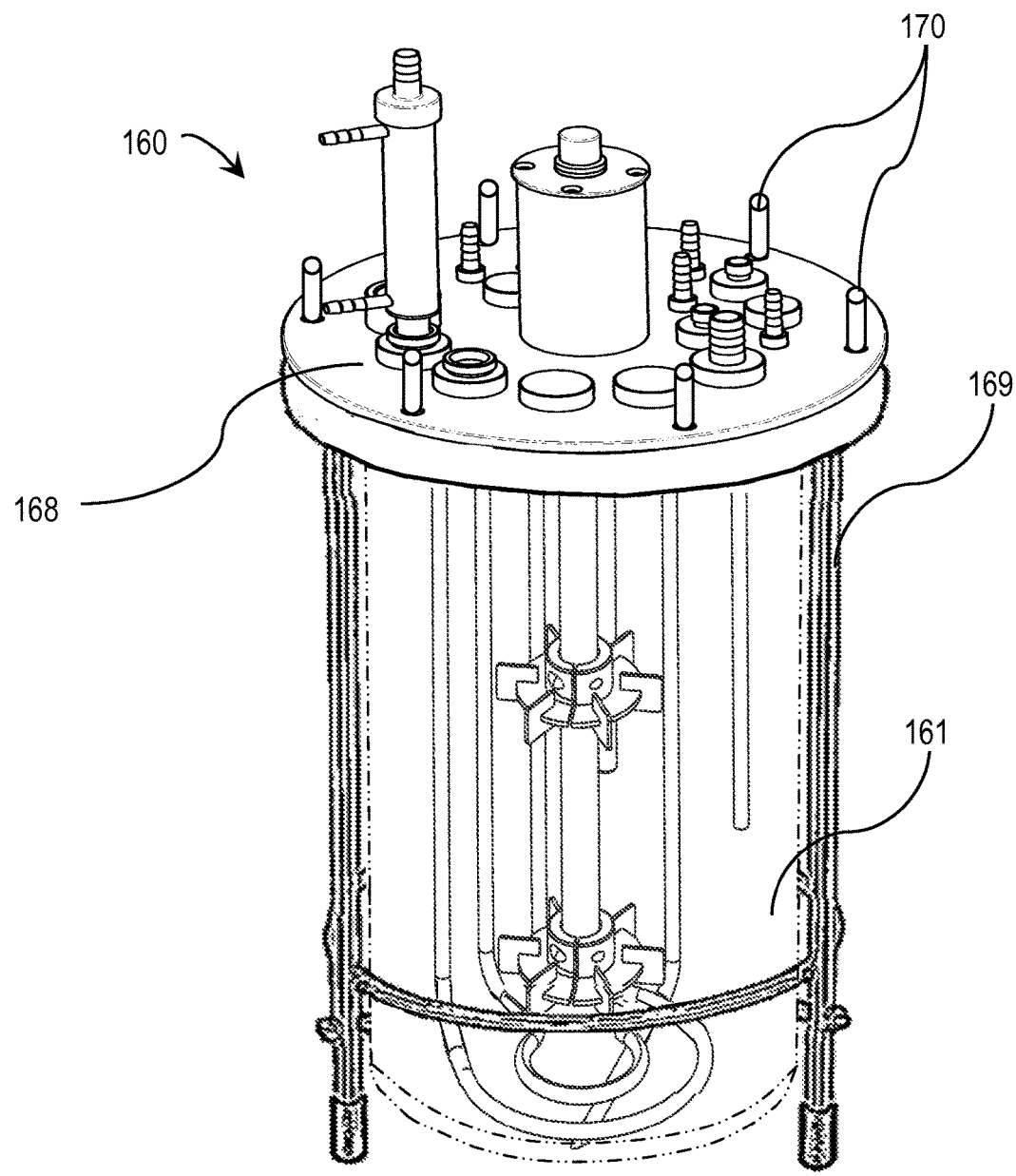
FIG. 6 shows a side perspective view of a conventional glass bioreactor.
Figure 7:
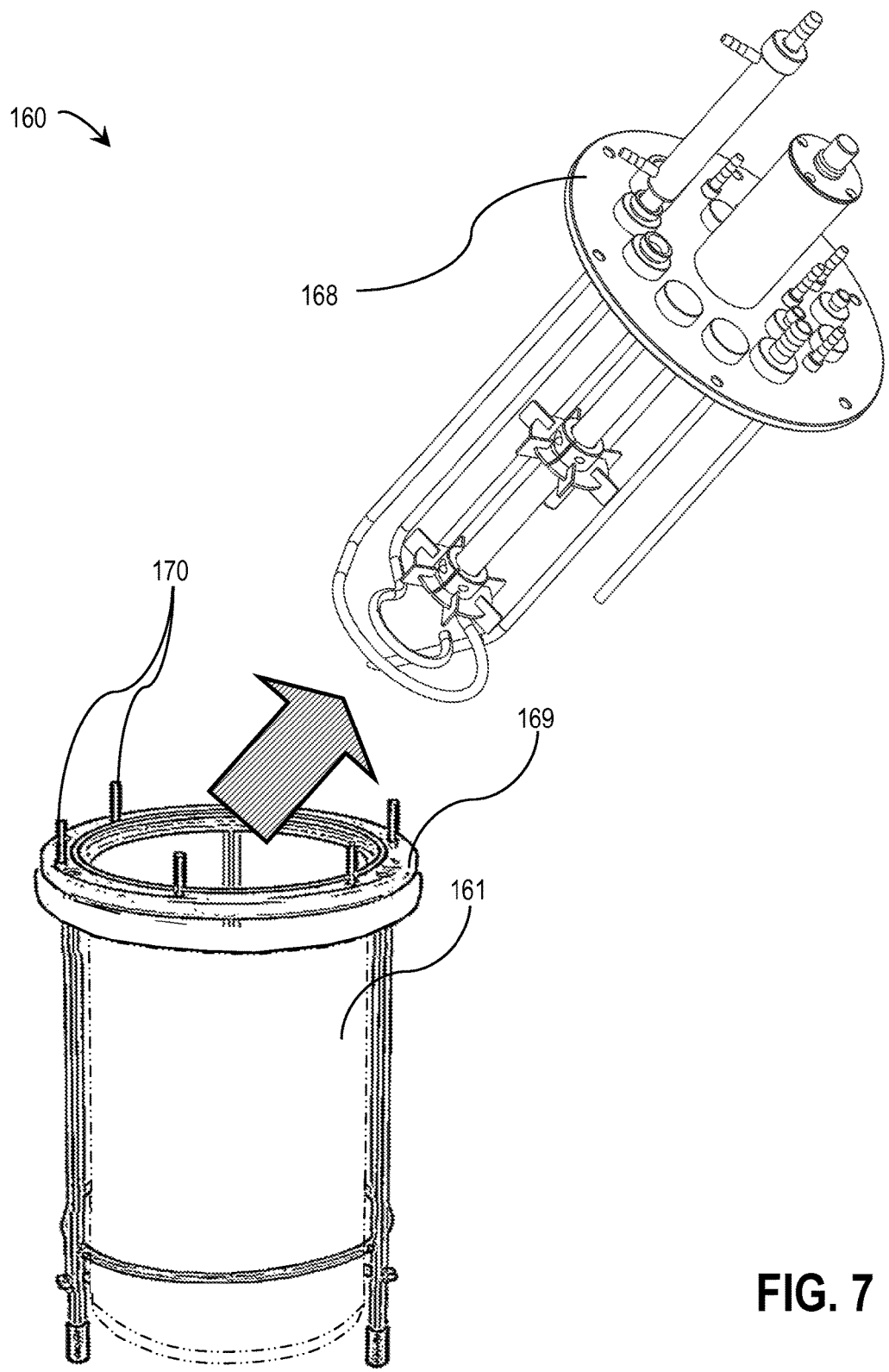
FIG. 7 shows side perspective view of the headplate and internal components of the conventional glass bioreactor being removed from the glass vessel.
Figure 8:
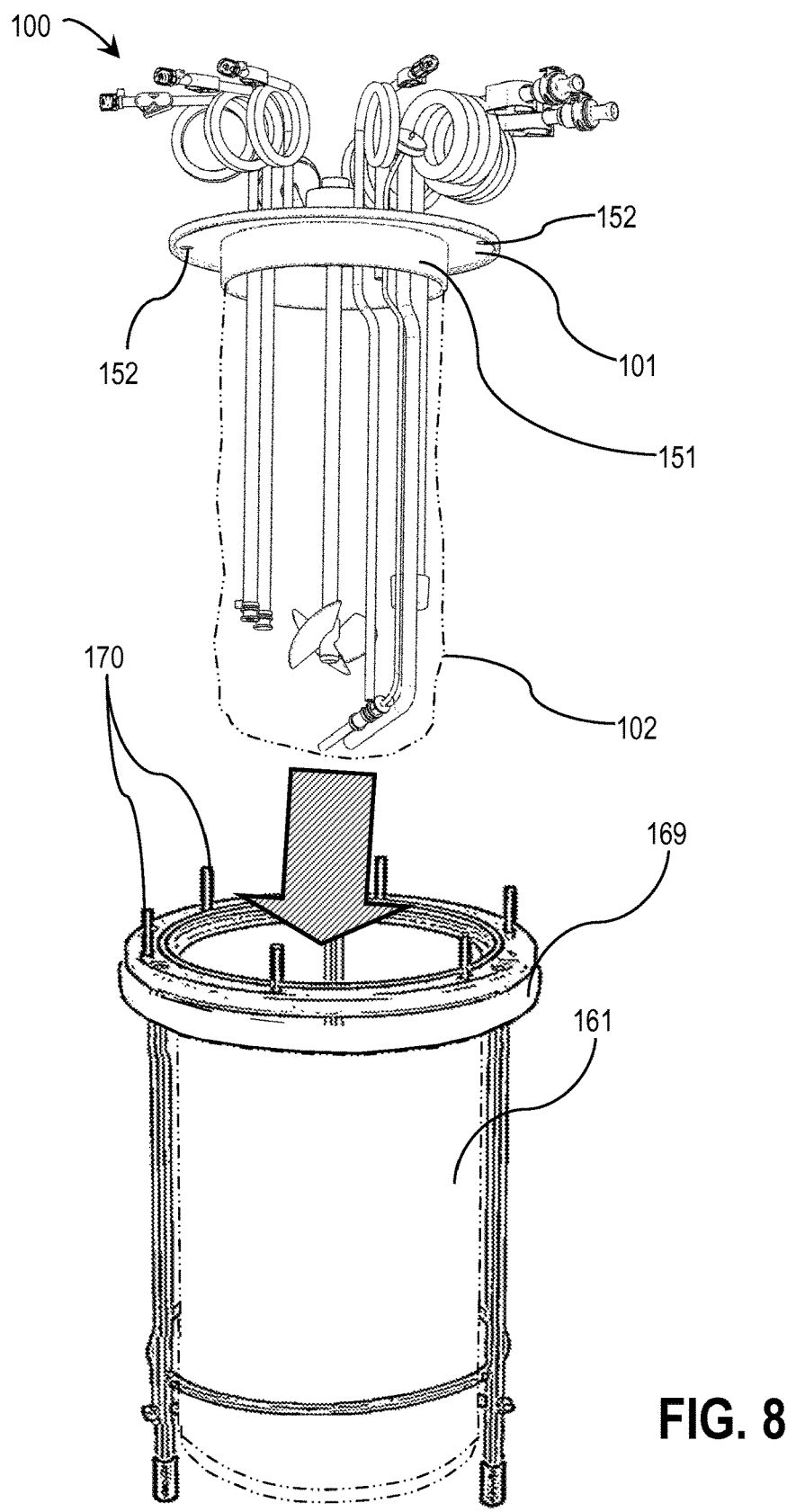
FIG. 8 shows a side perspective view of the disposable bioreactor of FIG. 1 being installed into the glass vessel of the conventional glass bioreactor.

As best seen in FIGS. 3, 4, and 6-8, headplate 101 has a cylindrical collar 151 formed on its underside and adapted to retain vessel liner 102. As shown in FIGS. 6-8, collar 151 is also adapted to fit within the upper opening of the glass vessel 161 of an existing conventional glass bioreactor 160, after the headplate 168 and internal components have been removed, thereby permitting disposable bioreactor 100 to replace these components and use the same glass vessel and stand 169. One or more apertures 152 of headplate 101 may be used to secure bioreactor 100 to stand 169, e.g., using screws or bolts 170. Bioreactor 100 can be placed in other types of rigid structures as well.

In one exemplary method for operating bioreactor 100, a culture medium is first loaded via one or more of addition tubes 136, 137 and the gas addition port. The impeller 109 is then activated by the external drive assembly, as described above, to begin stirring. Gas flow through sparger tube 106 is then initiated. Temperature within the bioreactor is controlled to a setpoint based on the reading of the temperature sensor (not shown) and with energy supplied by a device such as a external heater blanket (not shown). Dissolved oxygen is measured via DO probe (not shown), and pH is measured via pH sensor 123. The culture medium is seeded with cells, which are loaded, e.g., via one or more of addition tubes 136, 137. The culture medium is sampled via sampling tube 121. Once cell growth is complete, the cells are harvested via cell harvest tube 105. Other operations may take place in alternative embodiments and in connection with alternative applications for the use of bioreactor 100.

Thus, a bioreactor consistent with embodiments of the invention employs a hybrid design that includes features of both a bag-style design and a rigid plastic stirred-tank design. Headplate 101 may be rigid or elastomeric and is desirably joined to flexible vessel liner 102, e.g., by means of welding, mechanically fastening, elastomeric sealing, heat sealing, or the like. Vessel liner 102 is desirably sealed to headplate 101 so that the inside of vessel liner 102 remains sterile. Headplate 101 may also have shapes other than those illustrated or described herein.

Impeller 109 may, in alternative embodiments, include other types and configurations of stirring apparatus, including, e.g., a propeller-type impeller, a straight-blade impeller, and so forth. Accordingly, the term "stirrer" should be understood to include a motor-driven impeller as described herein, as well as other apparatus capable of stifling the culture medium inside the vessel liner.

Although not shown in the figures, other inlets, outlets, and ports may be employed in other embodiments. For example, a carbon dioxide sensor and/or a pressure sensor may be included.

Since a bioreactor consistent with embodiments of the invention generally employs the same types of connectors as conventional bioreactors and provides generally the same functionality, a scientist can utilize existing glass bioreactors and control systems that the scientist has already been using in an autoclave and convert those glass bioreactors and control systems to a single-use solution. Accordingly, the capital investment for the user is minimal to convert to the latest in bioreactor technology. In the process, the cleaning associated with prior-art bioreactors, as well as the need for sterilizing the bioreactor, are eliminated.

In addition, since the control system and geometry of the vessel remain the same as prior to conversion to a single-use solution, the user can continue to employ his or her existing protocols and recipes, saving on process-development time that would otherwise be required when working with a new bioreactor that has a different geometry and different control parameters.

Headplate 101 allows for many small ports and tubes to be placed in a small area, allowing this design to be feasibly used for vessel sizes below 1 liter. Accordingly, the limitation of conventional stirred-tank bag designs, wherein it is not possible to fit a sufficient number of ports in the bag to create a feasible bioreactor below 50 liters, is overcome by embodiments of the invention.

Embodiments of the invention also address the disposal and storage limitations that conventional rigid plastic stirred-tank designs pose. Since a large portion of the bioreactor (the vessel liner) is made of a flexible bag-type material, the single-use bioreactor can be compressed to a much smaller volume than its inflated volume, thus saving on storage space, packaging, and disposal costs.

Finally, this design allows the user to "plug-and-play" the use of a single-use bioreactor at any time. If the user chooses to revert to using the original glass bioreactor to compare runs, or simply because the user has run out of single-use vessels, the user can easily return to using his or her original equipment at any time.

Exemplary embodiments have been described wherein particular components perform particular functions. However, the particular functions may be performed by any suitable component and are not restricted to being performed by the particular components named in the exemplary embodiments.

Although the term "vessel liner" is used herein, it is not necessary that the vessel liner or bag actually be contained within a vessel or other equipment. For example, in one embodiment, bioreactor 100 is suspended from above, without the vessel liner being contained within any other structure. A vessel liner or bag used with bioreactor 100 can take many forms and can be flexible, rigid, or semi-rigid.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Unless explicitly stated otherwise, each numerical value and range should be interpreted as being approximate as if the word "about" or "approximately" preceded the value of the value or range. As used in this application, unless otherwise explicitly indicated, the term "connected" is intended to cover both direct and indirect connections between elements.

For purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. The terms "directly coupled," "directly connected," etc., imply that the connected elements are either contiguous or connected via a conductor for the transferred energy.

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

The invention claimed is:

1. A disposable bioreactor defining an interior volume having a circular top surface, a cylindrical side wall, and a bottom surface, the bioreactor comprising:
   a rigid headplate comprising a circular headplate disk defining a headplate disk plane, having a headplate disk diameter, and having a plurality of disk apertures formed therein;
   a flexible, cylindrical bag (a) having a circular bag opening and a cylindrical side wall having a bag diameter and (b) capable of receiving a culture medium, wherein:
   the side wall of the bag is sealingly and permanently coupled at the bag opening to the headplate such that the side wall of the bag is perpendicular to the headplate disk plane;
   the headplate disk diameter is larger than the bag diameter;
   a circular portion of the headplate having a diameter substantially equal to the bag diameter, forms the circular top surface of the bioreactor's interior volume;
   the bag forms the bottom surface and at least a portion of the cylindrical side wall of the bioreactor's interior volume:
   an extended portion of the headplate disk extends beyond the top surface of the bioreactor's interior volume in the headplate disk plane; and
   the extended portion of the headplate disk enables the bioreactor to be supported by a ring-shaped support structure having a diameter larger than the bag diameter, but smaller than the headplate disk diameter;
   tubing, for one or more of the disk apertures, extending from an outer side of the headplate disk through the corresponding disk aperture into the bioreactor's interior volume;
   an impeller shaft extending from the outer side of the headplate disk through a corresponding disk aperture into the bioreactor's interior volume;
   an impeller connected to an end of the impeller shaft inside the bioreactor's interior volume; and
   a drive assembly connected to the headplate disk on the outer side of the headplate disk and adapted to rotate the impeller shaft and the impeller.

2. The bioreactor of claim 1, wherein the tubing comprises at least one inlet tube passing through an inlet port aperture and at least one outlet tube passing through an output port aperture, wherein:
   the inlet tube is adapted to provide matter to the culture medium; and
   the outlet tube is adapted to extract matter from the culture medium.

3. The bioreactor of claim 1, further comprising a dissolved oxygen sensor coupled to and extending from the headplate, the dissolved oxygen sensor adapted to detect dissolved oxygen in the culture medium.

4. The bioreactor of claim 1, further comprising a temperature sensor coupled to and extending from the headplate, the temperature sensor adapted to detect temperature in the culture medium.

5. The bioreactor of claim 1, wherein the headplate comprises one or more apertures located and sized to accommodate bolts for securing the bioreactor to a stand of a conventional bioreactor.

6. The bioreactor of claim 1, further comprising an exhaust port coupled to a filter extending from the headplate, the exhaust port adapted to permit ventilation through the filter of gas from inside the bag.

7. The bioreactor of claim 1, further comprising a sparger port coupled to a filter extending from the headplate and to a sparger tube, the sparger tube adapted to receive a gas through the filter and to inject the gas into the culture medium.

8. The bioreactor of claim 1, wherein the drive assembly comprises an extended portion and a permanent magnet disposed within the extended portion and coupled to the impeller shaft, wherein, when a motor-driven magnet rotates around the extended portion, the permanent magnet is caused to rotate, thereby rotating the impeller shaft.

9. The bioreactor of claim 1, wherein:
the headplate further comprises a cylindrical headplate collar formed on an inner side of the headplate disk, defining a collar aperture, and having a cylindrical side wall having a headplate collar diameter smaller than the headplate disk diameter, the collar adapted to fit within the upper opening of the stand of a conventional bioreactor;
the bag diameter is substantially equal to the outer diameter of the headplate collar;
the side wall of the bag is parallel to the side wall of the headplate collar;
the inner surface of the headplate collar forms a portion of the interior surface of the cylindrical side wall of the bioreactor's interior volume with the bag forming the remainder of the interior surface of the cylindrical side wall of the bioreactor's interior volume; and
the impeller shaft and each tubing extends through the collar aperture on the inner side of the headplate disk.

10. The bioreactor of claim 9, wherein the bag is sealingly and permanently coupled to the headplate collar.

11. The bioreactor of claim 1, wherein the bag is welded to the headplate to provide a permanent coupling seal of the bag to the headplate.

12. The bioreactor of claim 1, wherein the bag is heat sealed to the headplate to provide a permanent coupling seal of the bag to the headplate.

13. The bioreactor of claim 1, wherein the bag is a flexible vessel liner that is configured to fit within a rigid structure of a bioreactor having a stand configured to be secured to the headplate.

14. The bioreactor of claim 13, wherein the rigid structure is a glass vessel of the bioreactor.

15. The bioreactor of claim 1, wherein at least one tubing comprises a coiled portion that permits extension on the outer side of the headplate disk.

16. The bioreactor of claim 1, wherein at least one tubing comprises a connector connected to an end of the tubing on the outer side of the headplate disk and adapted to mate the corresponding tubing to another component.

17. The bioreactor of claim 1, wherein at least one tubing comprising a tubing clamp connected to the tubing on the outer side of the headplate disk and adapted to selectively clamp the tubing.

18. The bioreactor of claim 1, wherein the bioreactor is configured to be suspended from above without the bag being contained within any other structure.

19. The bioreactor of claim 1, wherein:
the only access to the bioreactor's interior volume is through the disk apertures in the rigid headplate;
other than the bag's circular opening which is sealingly and permanently coupled to the headplate, the bag has no apertures that provide access to the bioreactor's interior volume; and
the cylindrical side wall and the bottom of the bioreactor's interior volume have no apertures that provide access to the bioreactor's interior volume.

20. The bioreactor of claim 1, further comprising:
a dissolved oxygen sensor coupled to and extending from the headplate, the dissolved oxygen sensor adapted to detect dissolved oxygen in the culture medium;
a temperature sensor coupled to and extending from the headplate, the temperature sensor adapted to detect temperature in the culture medium;
an exhaust port coupled to a filter extending from the headplate, the exhaust port adapted to permit ventilation through the filter of gas from inside the bag; and
a sparger port coupled to a filter extending from the headplate and to a sparger tube, the sparger tube adapted to receive a gas through the filter and to inject the gas into the culture medium, wherein:
the bioreactor is configured to be suspended from above without the bag being contained within any other structure;
the tubing comprises at least one inlet tube passing through an inlet port aperture and at least one outlet tube passing through an output port aperture;
the inlet tube is adapted to provide matter to the culture medium;
the outlet tube is adapted to extract matter from the culture medium;
the headplate further comprises a cylindrical headplate collar formed on an inner side of the headplate disk, defining a collar aperture, and having a cylindrical side wall having headplate collar diameter smaller than the headplate disk diameter, the collar adapted to fit within the upper opening of the stand of a conventional bioreactor;
the bag diameter is substantially equal to the outer diameter of the headplate collar;
the side wall of the bag is parallel to the side wall of the headplate collar;
the inner surface of the headplate collar forms a portion of the interior surface of the cylindrical side wall of the bioreactor's interior volume with the bag forming the remainder of the interior surface of the cylindrical side wall of the bioreactor's interior volume;
the impeller shaft and each tubing extends through the collar aperture on the inner side of the headplate disk;
the bag is sealingly and permanently coupled to the headplate collar;
the drive assembly comprises an extended portion and a permanent magnet disposed within the extended portion and coupled to the impeller shaft, wherein, when a motor-driven magnet rotates around the extended portion, the permanent magnet is caused to rotate, thereby rotating the impeller shaft;

the bag is welded or heat sealed to the headplate to provide a permanent coupling seal of the bag to the headplate;

the only acess to the bioreactor's interior volume is through the disk apertures in the rigid headplate;

other than the bag's circular opening which is sealingly and permanently coupled to the headplate, the bag has no apertures that provide access to the bioreactor's interior volume; and the cylindrical side wall and the bottom of the bioreactor's interior volume have no apertures that provide access to the bioreactor's interior volume.

* * * * *